(12) United States Patent
Kawano et al.

(10) Patent No.: US 10,004,691 B2
(45) Date of Patent: Jun. 26, 2018

(54) ORALLY DISINTEGRABLE TABLET

(71) Applicant: Takeda Pharmaceutical Company Limited, Osaka-shi, Osaka (JP)

(72) Inventors: Tetsuya Kawano, Osaka (JP); Yumiko Ishii, Osaka (JP)

(73) Assignee: Takeda Pharmaceuticals Company Limited, Osaka (JP)

( * ) Notice: Subject to any disclaimer, the term of this patent is extended or adjusted under 35 U.S.C. 154(b) by 0 days. days.

(21) Appl. No.: 14/891,930

(22) PCT Filed: May 20, 2014

(86) PCT No.: PCT/JP2014/063307
§ 371 (c)(1),
(2) Date: Nov. 17, 2015

(87) PCT Pub. No.: WO2014/189034
PCT Pub. Date: Nov. 27, 2014

(65) Prior Publication Data
US 2016/0089338 A1    Mar. 31, 2016

(30) Foreign Application Priority Data

May 21, 2013 (JP) ................................ 2013-107072

(51) Int. Cl.
| | |
|---|---|
| *A61K 9/20* | (2006.01) |
| *A61K 9/00* | (2006.01) |
| *A61K 31/4439* | (2006.01) |
| *A61K 31/616* | (2006.01) |
| *A61K 9/50* | (2006.01) |

(52) U.S. Cl.
CPC .......... *A61K 9/2081* (2013.01); *A61K 9/0056* (2013.01); *A61K 9/2018* (2013.01); *A61K 9/2027* (2013.01); *A61K 31/4439* (2013.01); *A61K 31/616* (2013.01); *A61K 9/5026* (2013.01); *A61K 9/5078* (2013.01); *A61K 9/5084* (2013.01)

(58) Field of Classification Search
CPC .. A61K 9/2081; A61K 31/616; A61K 9/2027; A61K 9/2018
See application file for complete search history.

(56) References Cited

U.S. PATENT DOCUMENTS

| | | | |
|---|---|---|---|
| 7,067,149 B1 | 6/2006 | Chauveau et al. | |
| 2004/0022846 A1* | 2/2004 | Depui | A61K 9/2081 424/452 |
| 2005/0249806 A1 | 11/2005 | Proehl et al. | |
| 2007/0122470 A1 | 5/2007 | Johansson et al. | |
| 2010/0297226 A1 | 11/2010 | Penhasi et al. | |
| 2010/0316709 A1* | 12/2010 | Kurasawa | A61K 9/0056 424/468 |
| 2012/0128764 A1 | 5/2012 | Venkatesh et al. | |
| 2013/0243859 A1 | 9/2013 | Mima et al. | |
| 2015/0132379 A1 | 5/2015 | Kawano | |

FOREIGN PATENT DOCUMENTS

| | | |
|---|---|---|
| EP | 1 726 301 | 11/2006 |
| JP | 11-501948 | 2/1999 |
| JP | 2002-087965 | 3/2002 |
| JP | 2002-529392 | 9/2002 |
| JP | 2006-528243 | 12/2006 |
| JP | 2007-522217 | 8/2007 |
| JP | 2009-517466 | 4/2009 |
| JP | 2009-519334 | 5/2009 |
| JP | 2009-256344 | 11/2009 |
| JP | 2009-538901 | 11/2009 |
| JP | 2012-518655 | 8/2012 |
| WO | 97/25064 | 7/1997 |
| WO | 99/59544 | 11/1999 |
| WO | 00/06126 | 2/2000 |
| WO | 2004/100857 | 11/2004 |
| WO | 2008/081891 | 7/2005 |
| WO | 2005/076987 | 8/2005 |
| WO | 2007/064274 | 6/2007 |
| WO | 2007/078271 | 7/2007 |
| WO | 2007/138606 | 12/2007 |
| WO | 2012/074110 | 6/2012 |
| WO | 2013/081177 | 6/2013 |
| WO | 2013/183497 | 12/2013 |

OTHER PUBLICATIONS

Extended European Search Report issued in corresponding European Patent Application No. 14800342.9, dated Dec. 8, 2016, 8 pages.
Lehmann, et al., "Fast Disintegrating Controlled Release Tablets from Coated Particles", Drugs made in German, vol. 37, No. 2, 1994, pp. 53-60.
International Search Report issued for PCT/JP2014/063307, 2 pages, dated Jul. 8, 2014.
EUDRAGIT L 30 D-55, Technical Information, Evonik Industries AG, Info 7.5/E, May 2014, pp. 1-6.

(Continued)

*Primary Examiner* — Jianfeng Song
(74) *Attorney, Agent, or Firm* — Hamre, Schumann, Mueller & Larson, P.C.

(57) ABSTRACT

Provided is an orally disintegrating tablet which shows high stability of the active ingredients (acetylsalicylic acid and PPI), and expresses the pharmacological effects of the active ingredients stably and rapidly after administration. A multiple-unit type orally disintegrating tablet containing enteric-coated micro granules containing acetylsalicylic acid, enteric-coated micro granules containing a proton pump inhibitor, and an additive, wherein an enteric coating layer of the enteric-coated micro granules containing acetylsalicylic acid contains an aqueous enteric polymer base and a sustained-release base.

8 Claims, No Drawings

(56) References Cited

OTHER PUBLICATIONS

Specifications and test methods for EUDRAGIT L 30 D-55, EVONIK Rohm GmbH, Info 7.5/E, Nov. 2007, pp. 1-5.

* cited by examiner

ORALLY DISINTEGRABLE TABLET

TECHNICAL FIELD

The present invention relates to a multiple-unit type orally disintegrating tablet containing a proton pump inhibitor (hereinafter sometimes to be referred to as PPI) and acetylsalicylic acid.

BACKGROUND OF THE INVENTION

It sometimes happens that low dose acetylsalicylic acid administered to suppress thrombus and/or embolization (antiplatelet therapy) in cerebrovascular and circulatory diseases induces gastric ulcer or duodenal ulcer. Since discontinuation of administration of acetylsalicylic acid may result in thrombus and/or embolization, it is considered important to continue administration of low dose acetylsalicylic acid while suppressing the onset of ulcer.

While acetylsalicylic acid is also known as a non-steroidal anti-inflammatory drug (NSAIDs), and mainly used for the treatment of pain, fever and inflammation, non-steroidal anti-inflammatory drug may cause gastric ulcer or duodenal ulcer. Particularly, in the treatment of rheumatoid arthritis, osteoarthritis and the like, discontinuation of administration of non-steroidal anti-inflammatory drug may be difficult, since it markedly degrades the quality of life (QOL). Therefore, it is considered important to continue administration of non-steroidal anti-inflammatory drug while suppressing the onset of ulcer.

On the other hand, since PPIs of benzimidazole compounds (e.g., lansoprazole, omeprazole and the like) have a strong gastric acid secretion-inhibitory action, a gastric mucosa-protective action and the like, they have been widely used as therapeutic agents for peptic ulcer and the like. Particularly, lansoprazole preparation has obtained an approval also in Japan in recent years on the efficacy of "suppression of onset of gastric ulcer or duodenal ulcer by administration of low dose acetylsalicylic acid" and "suppression of onset of gastric ulcer or duodenal ulcer by administration of non-steroidal anti-inflammatory drug", and a clinical effect of suppression of the onset of gastric ulcer or duodenal ulcer due to the dosing of acetylsalicylic acid has been demonstrated.

Patent document 1 (WO 97/25064) discloses a pharmaceutical dosage form for oral administration, which contains an acid susceptible proton pump inhibitor with at least one kind of non-steroidal anti-inflammatory drug and, when desired, a pharmaceutically acceptable excipient.

Patent document 2 (WO 2007/064274) discloses an oral pharmaceutical dosage form comprising, as active ingredients, an acid susceptible proton pump inhibitor together with acetyl salicylic acid or a derivative thereof and optionally pharmaceutically acceptable excipients, characterized in that the dosage form is in the form of an oral fixed combination dosage form comprising a group of separate physical units comprising the acid susceptible proton pump inhibitor and one or more other separate physical units comprising the acetyl salicylic acid or a derivative thereof, and wherein at least the proton pump inhibitor is protected by an enteric coating layer.

Patent document 3 (WO 2005/076987) discloses a pharmaceutical composition comprising: (a) a therapeutically effective amount of at least one acid labile proton pump inhibitor; (b) at least one buffering agent in an amount sufficient to increase gastric fluid pH to a pH that prevents acid degradation of at least some of the proton pump inhibitor in the gastric fluid; and (c) a therapeutically effective amount of at least one non-steroidal anti-inflammatory drug.

While PPI such as lansoprazole and the like and acetylsalicylic acid have already been commercially available as single agents, a multiple-unit type orally disintegrating tablet containing both PPI and acetylsalicylic acid is not known.

DOCUMENT LIST

Patent Documents patent document 1: WO 97/25064
patent document 2: WO 2007/064274
patent document 3: WO 2005/076987

SUMMARY OF THE INVENTION

Problems to be Solved by the Invention

Provision of a preparation containing both PPI and acetylsalicylic acid as active ingredients (combination agent) has extremely high clinical usefulness. However, practicalization of a preparation containing plural active ingredients is not easy as compared to preparations containing a single active ingredient. For example, the composition of the preparation needs to be controlled such that the dissolution rate of the active ingredient is optimized upon practicalization of the preparation, since the dissolution rate of the active ingredient from the preparation can influence the time-course efficacy profile after administration. In the case of a combination agent, however, the dissolution rate of each active ingredient needs to be optimized, and pharmaceutical difficulty is high. It is also necessary to suppress an adverse influence caused by interactions of plural active ingredients contained in a combination agent (decrease of preservation or chemical stability such as time-course decomposition of active ingredients, low activity and the like, decrease of dissolution stability such as time-course change of active ingredient dissolution pattern and the like, and the like).

Furthermore, the development of an orally disintegrating tablet that can be taken easily while maintaining the convenience for handling, which is the characteristic of tablet, and can be administered whenever necessary at anytime and anywhere with ease without water is desired along with the aging of the population and/or change of life environment.

The present inventors have conducted intensive studies and found that a multiple-unit type orally disintegrating tablet comprising enteric-coated micro granules containing acetylsalicylic acid, enteric-coated micro granules containing PPI, and an additive, wherein an enteric coating layer of the enteric-coated micro granules containing acetylsalicylic acid comprises an aqueous enteric polymer base and a sustained-release base, shows high stability of the active ingredients (acetylsalicylic acid and PPI), and expresses the pharmacological effects of the active ingredients stably and rapidly after administration, which resulted in the completion of the present invention.

Means of Solving the Problems

That is, the present invention provides the following.
[1] A multiple-unit type orally disintegrating tablet comprising enteric-coated micro granules containing acetylsalicylic acid, enteric-coated micro granules containing a proton pump inhibitor, and an additive, wherein an enteric coating layer of the enteric-coated micro granules containing acetylsalicylic acid comprises an aqueous enteric polymer base and a sustained-release base.

[2] The orally disintegrating tablet of the above-mentioned [1], wherein the aqueous enteric polymer base is a methacrylic acid copolymer LD.

[3] The orally disintegrating tablet of the above-mentioned [1], wherein the sustained-release base is an ethyl acrylate-methyl methacrylate copolymer.

[4] The orally disintegrating tablet of the above-mentioned [1], wherein the enteric coating layer of the enteric-coated micro granules containing acetylsalicylic acid contains the aqueous enteric polymer base and the sustained-release base at a solid content weight ratio of 80:20-95:5.

[5] The orally disintegrating tablet of the above-mentioned [1], wherein the enteric-coated micro granules containing acetylsalicylic acid have an average particle size of not more than 600 μm.

[6] The orally disintegrating tablet of the above-mentioned [1], wherein the content of acetylsalicylic acid is 70 mg-120 mg per tablet.

[7] The orally disintegrating tablet of the above-mentioned [1], wherein the content of acetylsalicylic acid in the enteric-coated micro granules containing acetylsalicylic acid is about 20-about 80 wt %.

[8] The orally disintegrating tablet of the above-mentioned [1], wherein the additive contains sugar alcohol.

[9] The orally disintegrating tablet of the above-mentioned [8], wherein the sugar alcohol is mannitol.

[10] The orally disintegrating tablet of the above-mentioned [8], wherein the content of sugar alcohol is about 40-about 90 wt % of the total weight of the component contained in the part other than the enteric-coated micro granules containing acetylsalicylic acid and enteric-coated micro granules containing a proton pump inhibitor.

[11] The orally disintegrating tablet of the above-mentioned [1], wherein the proton pump inhibitor is lansoprazole, omeprazole, rabeprazole, pantoprazole or an optically active form thereof or a salt thereof.

[12] The orally disintegrating tablet of the above-mentioned [1], wherein the acetylsalicylic acid and the proton pump inhibitor each show an acid resistance rate of not more than 10%.

[13] The orally disintegrating tablet of the above-mentioned [1], wherein the additive is free of an antacid and a foaming agent.

[14] The orally disintegrating tablet of the above-mentioned [1], having an oral disintegration time of within about 60 seconds.

Effect of the Invention

The orally disintegrating tablet of the present invention can be administered for the treatment or suppression of the onset of gastric ulcer or duodenal ulcer while continuing administration of acetylsalicylic acid, since it contains (1) PPI having a strong acid secretion suppressive action and (2) acetylsalicylic acid useful as a prophylactic and/or therapeutic agent for cerebrovascular or circulatory diseases, for example, a thrombus and/or embolization inhibitor for angina pectoris (chronic stable angina pectoris, unstable angina pectoris), myocardial infarction; a prophylactic and/or therapeutic agent for ischemic cerebrovascular disorder (transient ischemic attack (TIA), cerebral infarction); a thrombus and/or embolization inhibitor used after coronary-artery bypass surgery (CABG) or percutaneous transluminal coronary angioplasty (PTCA); or a prophylactic and/or therapeutic agent for Kawasaki disease (including cardiovascular sequelae due to Kawasaki disease).

Moreover, since acetylsalicylic acid can also be used as one kind of non-steroidal anti-inflammatory drug for the treatment of mainly pain, fever and inflammation, the orally disintegrating tablet of the present invention can be administered for the treatment or suppression of the onset of gastric ulcer or duodenal ulcer while continuing administration of a non-steroidal anti-inflammatory drug.

The orally disintegrating tablet of the present invention shows high stability of the active ingredients (acetylsalicylic acid and PPI), and expresses a pharmacological effect of the active ingredients stably and rapidly after administration.

The orally disintegrating tablet of the present invention can be easily administered while maintaining the convenience for handling, and can be administered whenever necessary at anytime and anywhere with ease without water.

The orally disintegrating tablet of the present invention is superior in tablet strength, dissolution property of active ingredients (acetylsalicylic acid and PPI), preservation stability and acid resistance.

BRIEF DESCRIPTION OF THE DRAWINGS

The present invention is explained in detail in the following.

One of the characteristics of the orally disintegrating tablet of the present invention is of a multiple-unit type.

Generally, a "multiple-unit type" tablet contains plural units (e.g., micro granules), and individual units have functions as a preparation such as release control and enteric coating. The plural units each independently exhibit preparation functions even when used alone. That is, two or more individual units, for example, respective micro granules have, in addition to the active ingredients, functions as a preparation such as enteric coating and the like. The preparation function as used herein is not limited to a single function. For example, multiple-unit type groups having different preparation functions, for example, plural preparation functions such as release control and enteric function can also be combined. In the multiple-unit type, the administered tablet is rapidly disintegrated to release micro granules, and the released micro granules show the above-mentioned preparation functions.

The multiple-unit type orally disintegrating tablet of the present invention is characterized in that it contains "enteric-coated micro granules containing acetylsalicylic acid", "enteric micro granules containing PPI" and "additive", and the enteric coating layer of the "enteric-coated micro granules containing acetylsalicylic acid" contains an aqueous enteric polymer base and a sustained-release base.

(1) "Enteric-Coated Micro Granules Containing Acetylsalicylic Acid"

In the present invention, the "enteric-coated micro granules containing acetylsalicylic acid" means micro granules wherein a "composition containing acetylsalicylic acid" (composition before coating with an enteric coating layer) is coated with an enteric coating layer.

The "coating" means also partial coating and adhesion or adsorption in addition to coating the whole surface of an object (e.g., core) which is to be coated. In the present specification, the "average particle size" means volume based distribution median size (median size: 50% particle size from cumulative distribution), unless otherwise specified. It can be measured by, for example, a laser diffraction particle distribution measurement method. Concretely exemplified is a method using Laser Diffraction Analyzer, type: HERDS RODOS [trade name; manufactured by Sympatec (Germany)].

The "enteric-coated micro granules containing acetylsalicylic acid" have an average particle size of generally not more than 600 μm, preferably 200-500 μm, more preferably 200-450 μm.

The orally disintegrating tablet of the present invention having an average particle size within the above-mentioned range tastes nice since a rough feeling on oral disintegration of the orally disintegrating tablet is less.

The content of acetylsalicylic acid in the orally disintegrating tablet of the present invention is generally about 70 mg-about 400 mg per one orally disintegrating tablet. When the non-steroidal anti-inflammatory drug is mainly used for the treatment of pain, fever or inflammation, the content of acetylsalicylic acid in the orally disintegrating tablet of the present invention is generally about 240 mg-about 400 mg per one orally disintegrating tablet. On the other hand, when used for the suppression of thrombus and/or embolization and the like in cerebrovascular or circulatory diseases (antiplatelet therapy), the content of acetylsalicylic acid in the orally disintegrating tablet of the present invention is generally about 70 mg-about 120 mg, preferably about 100 mg, per one orally disintegrating tablet.

The content of acetylsalicylic acid in the "enteric-coated micro granules containing acetylsalicylic acid" is generally about 20-about 80 wt %, preferably about 30-about 80 wt %, more preferably about 40-about 80 wt %.

As acetylsalicylic acid, acetylsalicylic acid powder, acetylsalicylic acid granules, or a premix of acetylsalicylic acid and an excipient (e.g., acetylsalicylic acid:cornstarch=90:10 dry-type granulation product) may be used. Examples of the commercially available product include Rhodine 3220 (trade name; manufactured by Rhodia). Examples of the granules include Rhodine 3118 (trade name; manufactured by Rhodia).

The "composition containing acetylsalicylic acid" may contain additives such as a water-soluble polymer (e.g., hydroxypropylmethylcellulose (hereinafter sometimes to be abbreviated as HPMC) (TC-5E (trade name; manufactured by Shin-Etsu Chemical Co., Ltd.))), a binder (hydroxypropylcellulose (hereinafter sometimes to be abbreviated as HPC)), as well as disintegrants (e.g., low-substituted hydroxypropylcellulose (hereinafter sometimes to be abbreviated as L-HPC) (LH-32 (trade name; manufactured by Shin-Etsu Chemical Co., Ltd.)), excipients (e.g., mannitol, lactose, crystalline cellulose) and the like, which are generally used for the production of preparations. Examples of the additives include those exemplified as the below-mentioned "component contained in the part other than the enteric-coated micro granules". The amount thereof to be added is an amount generally used for the production of preparations.

The content of the "water-soluble polymer" in the "composition containing acetylsalicylic acid" is generally about 0-about 15 wt %. The content of the "disintegrant" in the "composition containing acetylsalicylic acid" is generally about 0-about 15 wt %. The content of the "excipient" in the "composition containing acetylsalicylic acid" is generally about 0-about 30 wt %.

Examples of the "enteric coating component" used to coat "a composition containing acetylsalicylic acid" include aqueous enteric polymer bases such as cellulose acetate phthalate (CAP (trade name; manufactured by Aquateric FMC)), hydroxypropylmethylcellulose phthalate (HP-55 (trade name; manufactured by Shin-Etsu Chemical Co., Ltd.)), hydroxymethylcellulose acetate succinate, methacrylic acid copolymer (e.g., methacrylic acid copolymer LD (Eudragit L30D-55 (trade name; manufactured by EVONIK INDUSTRIES)), Kollicoat MAE30DP (trade name; manufactured by BASF), Polyquid PA30 (trade name; manufactured by Sanyo Chemical Industries Ltd.) and the like), carboxymethylethylcellulose, shellac and the like; sustained-release bases such as methacrylate copolymer (e.g., ethyl acrylate-methyl methacrylate copolymer (Eudragit NE30D (trade name; manufactured by EVONIK INDUSTRIES)), aminoalkylmethacrylate copolymer RS (Eudragit RL30D (trade name; manufactured by EVONIK INDUSTRIES)), Ammonioalkyl Methacrylate Copolymer Dispersion, Type A (Eudragit RS30D (trade name; manufactured by EVONIK INDUSTRIES)) and the like) and the like; water-soluble polymers such as ethanol-soluble water-soluble polymer (e.g., cellulose derivatives such as HPC and the like, polyvinylpyrrolidone and the like), ethanol-insoluble water-soluble polymer (e.g., cellulose derivatives such as HPMC, methylcellulose, carmellose sodium and the like, sodium polyacrylate, polyvinyl alcohol, sodium alginate, guar gum and the like) and the like; plasticizers such as triethyl citrate, polyethylene glycol (e.g., polyethylene glycol 6000), acetylated monoglyceride, triacetin, castor oil and the like; corrigents such as citric anhydride and the like, lubricants such as glycerol monostearate, polysorbate 80 and the like, colorants such as yellow ferric oxide, red ferric oxide, titanium oxide and the like, and the like. These may be used alone or two or more kinds thereof may be used in combination.

As the aforementioned "aqueous enteric polymer base", methacrylic acid copolymers such as methacrylic acid copolymer LD and the like are preferable. The content of the "aqueous enteric polymer base" as a solid content is generally about 20-about 80 wt %, preferably about 40-about 80 wt %, more preferably about 50-about 80 wt %, of the "enteric coating layer".

While the aforementioned "sustained-release base" is generally used for imparting sustained releaseability to coated granules, it is used for reducing an impact on coated granules during tableting and maintaining acid resistance in the present invention. Therefore, the aforementioned "sustained-release base" can be rephrased as a "base for imparting plasticity" in the present invention, and preferred as such "sustained-release base" ("base for imparting plasticity") are methacrylate copolymers such as ethyl acrylate-methyl methacrylate copolymer and the like. The solid content of the "sustained-release base" is generally about 5-about 40 wt %, preferably about 5-about 30 wt %, more preferably about 5-about 25 wt %, of the "enteric coating layer".

The content of the aforementioned "plasticizer" is generally about 1-about 30 wt % of the "enteric coating layer". The content of the "plasticizer" is preferably about 2-about 20 parts by weight per 100 parts by weight of the aqueous enteric polymer base.

The content of the aforementioned "corrigent" is generally 0-about 5 wt % of the "enteric coating layer".

The content of the aforementioned "lubricant" is generally about 1-about 10 wt % of the "enteric coating layer".

The content of the aforementioned "colorant" is generally 0-about 5 wt % of the "enteric coating layer".

The "enteric coating layer" preferably contains an aqueous enteric polymer base and a sustained-release base and, for example, a preferable content ratio of methacrylic acid copolymer such as methacrylic acid copolymer LD and the like, and methacrylate copolymer such as ethyl acrylate-methyl methacrylate copolymer and the like (methacrylic acid copolymer (particularly, methacrylic acid copolymer LD): methacrylate copolymer (particularly, ethyl acrylate-methyl methacrylate copolymer)) is 80:20-95:5 as a weight ratio of the solid contents.

When the ratio of the sustained-release base becomes high, the dissolution tends to be slow, and when it becomes small, acid resistance tends to be not securable. In the present invention, a preparation superior in both the dissolution property and acid resistance of the active ingredients can be provided by setting the ratio of the aqueous enteric polymer base (methacrylic acid copolymer) and the sustained-release base (methacrylate copolymer) to fall within the above-mentioned range.

The "composition containing acetylsalicylic acid" can be produced by a known granulation method.

The "granulation method" includes, for example, tumbling granulation method (e.g., centrifugal tumbling granulation, etc.), fluid-bed granulation method (e.g., tumbling fluid-bed granulation, fluidized granulation, etc.), stirring granulation method and the like. Among others, preferred is fluid-bed granulation method, more preferred is tumbling fluid-bed granulation method.

Concrete example of the "tumbling granulation method" includes a method using "CF apparatus" manufactured by Freund Industrial Co., Ltd. and the like. Concrete examples of the "tumbling fluid-bed granulation method" include methods using "SPIR-A-FLOW" manufactured by Freund Corporation, "Multiplex" manufactured by Powrex Corp., "New-Marumerizer" manufactured by Fuji Paudal Co., Ltd., and the like. The method for spraying the mixed liquid mentioned below can be suitably selected in accordance with the kind of granulator, and may be, for example, any one of a top spray method, a bottom spray method, a tangential spray method, and the like. Among others, a tangential spray method is preferred.

The "composition containing acetylsalicylic acid" is produced by, for example, coating a core containing crystalline cellulose and lactose with acetylsalicylic acid.

For example, employed is a method described in JP-A-5-92918 (coating method), which comprises coating a core comprising crystalline cellulose and lactose with acetylsalicylic acid and, where necessary, binders, lubricants, excipients, a water-soluble polymer, etc. (hereinafter sometimes to be abbreviated as "coating layer"). For example, employed is a method which comprises coating a core with acetylsalicylic acid, and then further with binders, lubricants, excipients, a water-soluble polymer, and the like.

As the "composition containing acetylsalicylic acid", for example, acetylsalicylic acid itself can also be used alone. For example, crude particles of a dry granulation product of acetylsalicylic acid can be sieved and used as they are. Examples of the granulation product include Rhodine 3118 (trade name; manufactured by Rhodia).

In addition, an acetylsalicylic acid powder can be used singly, or spherical granules obtained by tumbling granulation of a mixture thereof with an excipient such as crystalline cellulose, cornstarch and the like, and the like can also be used.

Concrete example of the "tumbling granulation method" includes a method using "CF apparatus" manufactured by Freund Industrial Co., Ltd. and the like. Concrete examples of the "tumbling fluid-bed granulation method" include methods using "SPIR-A-FLOW" manufactured by Freund Corporation, "Multiplex" manufactured by Powrex Corp., "New-Marumerizer" manufactured by Fuji Paudal Co., Ltd., and the like.

The average particle size of the "cores" is about 250 μm or less, preferably about 50 to about 250 μm, more preferably about 100 to about 250 μm, especially preferably about 100 to about 200 μm. The "cores" having the above average particle size include particles which all pass through a sieve No. 50 sieve (300 μm), particles where about 5 w/w % or less of the total remain on a sieve No. 60 sieve (250 μm), and particles where about 10 w/w % or less of the total pass through a sieve No. 282 sieve (53 μm). The specific volume of the "core" is about 5 ml/g or less, preferably about 3 ml/g or less.

Examples of the "core" include (1) a spherical granulated product comprising crystalline cellulose and lactose, (2) a spherical granulated product being about 150 to about 250 μm and comprising crystalline cellulose (Avicel SP, manufactured by Asahi Chemical Co., Ltd.), (3) a stirring granulated product being about 50 to about 250 μm and comprising lactose (9 parts) and pregelatinized starch (1 part), (4) a micro particle being about 250 μm or less classified as a spherical granule composed of crystalline cellulose described in JP-A-61-213201, (5) a processed product such as wax formed to a sphere by spray chilling or melting granulation, (6) a processed product such as gelatin beads comprising oil component, (7) calcium silicate, (8) starch, (9) a porous particle such as chitin, cellulose, chitosan, etc, and (10) a bulk product such as granulated sugar, crystalline lactose, crystalline cellulose or sodium chloride, and processed preparations thereof. Further, these cores may be produced in accordance with per se known grinding method or granulation method, and sifted to prepare the particles having the desired particle size.

The above "spherical granulated product comprising crystalline cellulose and lactose" includes, for example, (i) a spherical granulated product being about 100 to about 200 μm and comprising crystalline cellulose (3 parts) and lactose (7 parts) [e.g., Nonpareil 105 (70-140) (particle size of about 100 to about 200 μm), manufactured by Freund Industrial Co., Ltd.], (ii) a spherical granulated product being about 150 to about 250 μm and comprising crystalline cellulose (3 parts) and lactose (7 parts) [e.g., Nonpareil NP-7:3, manufactured by Freund Industrial Co., Ltd.], (iii) a spherical granulated product being about 100 to about 200 μm and comprising crystalline cellulose (4.5 parts) and lactose (5.5 parts) [e.g., Nonpareil 105T (70-140) (particle size of about 100 to about 200 μm), manufactured by Freund Industrial Co., Ltd.], (iv) a spherical granulated product being about 150 to about 250 μm and comprising crystalline cellulose (5 parts) and lactose (5 parts) [e.g., Nonpareil NP-5:5, manufactured by Freund Industrial Co., Ltd.], and the like.

In order to produce a preparation which is superior in dissolution while retaining suitable strength, the "core" includes preferably the spherical granulated product comprising crystalline cellulose and lactose, more preferably the spherical granulated material comprising crystalline cellulose and lactose and containing 50 wt % or more of lactose. Among others, preferred is a core comprising 40 to 50 wt % of crystalline cellulose and 50 to 60 wt % of lactose.

The "core" employed in the present invention is preferably the spherical granulated product comprising crystalline cellulose and lactose, more preferably the spherical granulated product being about 100 to about 200 μm and comprising crystalline cellulose (4.5 parts) and lactose (5.5 parts).

The "core" may contain acetylsalicylic acid. Even when the core does not contain acetylsalicylic acid, the releaseability of acetylsalicylic acid can be controlled by a coating layer containing acetylsalicylic acid.

The "core" may be a powdery core, and is preferably as uniform a sphere as possible to reduce variability of the coating.

The ratio of the "coating layer" to the "core" can be selected within the range in which it is possible to control dissolution of acetylsalicylic acid and particle size of the composition, for example, generally about 50 to about 500 parts by weight per 100 parts by weight of the core.

The "coating layer" may be constructed by plural layers. At least one layer of the plural layers must contain acetylsalicylic acid. The combination of various layers such as a coating layer not containing the active ingredient, a base coating layer, and an enteric coating layer which constitute the coating layer can be suitably selected.

When the "core" is coated, for example, acetylsalicylic acid and the water-soluble polymer can be used as a mixed liquid. The liquid may be a solution or a dispersion, and can be prepared by using water or an organic solvent such as ethanol or an admixture thereof.

The concentration of the water-soluble polymer in the liquid varies according to the proportion of acetylsalicylic acid and the additives, and is generally about 0.1 to about 50 wt %, preferably about 0.5 to about 10 wt %, in order to retain the binding strength of acetylsalicylic acid to the core and maintain the viscosity of the liquid so as not to reduce the workability.

Where the coating layer comprises plural layers, the concentration of acetylsalicylic acid in each layer may be changed successively or gradually by selecting for the content proportion or viscosity of the water-soluble polymer or by successive coating with mixed liquid varying in the proportion of acetylsalicylic acid and the other additives. In the above case, it may be coated with a mixed liquid in which the content proportion of the water-soluble polymer is out of the range of about 0.1 to about 50 wt %, as long as the coating layer as a whole contains about 0.1 to about 50 wt % of the water-soluble polymer. Further, in forming the inactive coat according to known methods, the coating layer may comprise some layers such that the inactive layer may block each layer containing acetylsalicylic acid.

The above-mentioned coated product is dried and sieved to give a composition having a uniform particle size. Since the shape of the composition generally corresponds to the core, an about spherical composition can also be obtained. As the sieve, for example, No. 50 (300 μm) round sieve can be used, and the composition is obtained by passing the product through the No. 50 round sieve.

A uniform coating can be applied by matching the size of the "composition containing acetylsalicylic acid", which contributes to the acid resistance (preferably, not more than 10%).

The "enteric micro granules containing acetylsalicylic acid" can be produced according to a granulation method similar to the above, for example, a method which comprises coating a composition containing acetylsalicylic acid with an enteric coating layer, in order to protect acetylsalicylic acid or to impart enteric dissolution. If necessary, the composition containing acetylsalicylic acid coated with an enteric coating layer may be further coated by a water-soluble sugar alcohol, preferably mannitol. In such case, the strength of the orally disintegrating tablet comprising the micro granules is improved.

The "enteric coating layer" is a layer having preferably about 20 to about 70 μm, more preferably about 30 to about 50 μm of thickness and coating the whole surface of the composition containing acetylsalicylic acid. Therefore, the smaller the particle size of the composition is, the higher the wt % of the enteric coating layer in the whole micro granule becomes. In the "enteric micro granules containing acetylsalicylic acid", the "enteric coating layer" is generally about 10 to about 70 wt %, preferably about 20 to about 60 wt %, of the micro granule as a whole.

The enteric coating layer may be composed of plural (e.g., 2 or 3) layers.

(2) "Enteric Micro Granules Containing PPI"
(2)-1: PPI

In the present invention, a compound represented by the following formula (I) [hereinafter to be sometimes simply referred to as compound (I)] or an optically active form thereof or a salt thereof is preferable as PPI.

A compound represented by the formula (I):

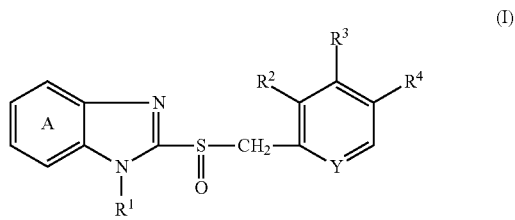

wherein ring A is a benzene ring optionally having substituent(s), $R^1$ is a hydrogen atom, an aralkyl group optionally having substituent(s), an acyl group or an acyloxy group, $R^2$, $R^3$ and $R^4$ are the same or different and each is a hydrogen atom, an alkyl group optionally having substituent(s), an alkoxy group optionally having substituent(s) or an amino group optionally having substituent(s), and Y is a nitrogen atom or CH, or an optically active form thereof, or a salt thereof.

In the above-mentioned compound (I), examples of the "substituent" of the "benzene ring optionally having substituent(s)" for ring A include a halogen atom, a cyano group, a nitro group, an alkyl group optionally having substituent(s), a hydroxy group, an alkoxy group optionally having substituent(s), an aryl group, an aryloxy group, a carboxy group, an acyl group, an acyloxy group, a 5- to 10-membered heterocyclic group and the like. The benzene ring may be substituted by about 1 to 3 of these substituents. When the number of substituents is two or more, each substituent may be the same or different. Of these substituents, a halogen atom, an alkyl group optionally having substituent(s), an alkoxy group optionally having substituent(s) and the like are preferable.

Examples of the halogen atom include fluorine, chlorine, bromine atom and the like. Of these, a fluorine atom is preferable.

Examples of the "alkyl group" of the "alkyl group optionally having substituent(s)" include a $C_{1-7}$ alkyl group (e.g., methyl, ethyl, propyl, isopropyl, butyl, isobutyl, sec-butyl, tert-butyl, pentyl, hexyl, heptyl group etc.) and the like. Examples of the "substituent" of the "alkyl group optionally having substituent(s)" include a halogen atom, a hydroxy group, a $C_{1-6}$ alkoxy group (e.g., methoxy, ethoxy, propoxy, butoxy etc.), a $C_{1-6}$ alkoxy-carbonyl group (e.g., methoxycarbonyl, ethoxycarbonyl, propoxycarbonyl etc.), a carbamoyl group and the like, and the number of these substituents may be about 1 to 3. When the number of substituents is two or more, each substituent may be the same or different.

Examples of the "alkoxy group" of the "alkoxy group optionally having substituent(s)" include a $C_{1-6}$ alkoxy group (e.g., methoxy, ethoxy, propoxy, isopropoxy, butoxy, isobutoxy, pentoxy etc.) and the like. Examples of the "substituent" of the "alkoxy group optionally having substituent(s)" include those similar to the "substituent" of the above-mentioned "alkyl group optionally having substituent(s)", and the number of substituents is the same.

Examples of the "aryl group" include a $C_{6-14}$ aryl group (e.g., phenyl, 1-naphthyl, 2-naphthyl, biphenyl, 2-anthryl etc.) and the like.

Examples of the "aryloxy group" include a $C_{6-14}$ aryloxy group (e.g., phenyloxy, 1-naphthyloxy, 2-naphthyloxy etc.) and the like.

Examples of the "acyl group" include formyl, alkylcarbonyl, alkoxycarbonyl, carbamoyl, alkylcarbamoyl, alkylsulfinyl, alkylsulfonyl and the like.

Examples of the "alkylcarbonyl group" include a $C_{1-6}$ alkyl-carbonyl group (e.g., acetyl, propionyl etc.) and the like.

Examples of the "alkoxycarbonyl group" include a $C_{1-6}$ alkoxy-carbonyl group (e.g., methoxycarbonyl, ethoxycarbonyl, propoxycarbonyl, butoxycarbonyl etc.) and the like.

Examples of the "alkylcarbamoyl group" include an N—$C_{1-6}$ alkyl-carbamoyl group (e.g., methylcarbamoyl, ethylcarbamoyl group etc.), an N,N-di-$C_{1-6}$ alkyl-carbamoyl group (e.g., N,N-dimethylcarbamoyl, N,N-diethylcarbamoyl etc.) and the like.

Examples of the "alkylsulfinyl group" include a $C_{1-7}$ alkylsulfinyl group (e.g., methylsulfinyl, ethylsulfinyl, propylsulfinyl, isopropylsulfinyl etc.) and the like.

Examples of the "alkylsulfonyl group" include a $C_{1-7}$ alkylsulfonyl group (e.g., methylsulfonyl, ethylsulfonyl, propylsulfonyl, isopropylsulfonyl etc.) and the like.

Examples of the "acyloxy group" include alkylcarbonyloxy, alkoxycarbonyloxy, carbamoyloxy, alkylcarbamoyloxy, alkylsulfinyloxy, alkylsulfonyloxy and the like.

Examples of the "alkylcarbonyloxy group" include a $C_{1-6}$ alkyl-carbonyloxy group (e.g., acetyloxy, propionyloxy etc.) and the like.

Examples of the "alkoxycarbonyloxy group" include a $C_{1-6}$ alkoxy-carbonyloxy group (e.g., methoxycarbonyloxy, ethoxycarbonyloxy, propoxycarbonyloxy, butoxycarbonyloxy etc.) and the like.

Examples of the "alkylcarbamoyloxy group" include a alkyl-carbamoyloxy group (e.g., methylcarbamoyloxy, ethylcarbamoyloxy etc.) and the like.

Examples of the "alkylsulfinyloxy group" include a $C_{1-7}$ alkylsulfinyloxy group (e.g., methylsulfinyloxy, ethylsulfinyloxy, propylsulfinyloxy, isopropylsulfinyloxy etc.) and the like.

Examples of the "alkylsulfonyloxy group" include a $C_{1-7}$ alkylsulfonyloxy group (e.g., methylsulfonyloxy, ethylsulfonyloxy, propylsulfonyloxy, isopropylsulfonyloxy etc.) and the like.

Examples of the "5- to 10-membered heterocyclic group" include a 5- to 10-membered (preferably 5- or 6-membered) heterocyclic group containing, besides carbon atom, one or more (e.g., 1-3) hetero atoms selected from nitrogen atom, sulfur atom and oxygen atom and the like. Specific examples include 2- or 3-thienyl group, 2-, 3- or 4-pyridyl group, 2- or 3-furyl group, 1-, 2- or 3-pyrrolyl group, 2-, 3-, 4-, 5- or 8-quinolyl group, 1-, 3-, 4- or 5-isoquinolyl group, 1-, 2- or 3-indolyl group and the like. Of these, preferred is a 5- or 6-membered heterocyclic group such as 1-, 2- or 3-pyrrolyl group and the like.

Preferably, ring A is a benzene ring optionally having 1 or 2 substituents selected from a halogen atom, an optionally halogenated $C_{1-4}$ alkyl group, an optionally halogenated $C_{1-4}$ alkoxy group and a 5- or 6-membered heterocyclic group.

Examples of the "aralkyl group" of the "aralkyl group optionally having substituent(s)" for $R^1$ include a $C_{7-16}$ aralkyl group (e.g., $C_{6-10}$ aryl $C_{1-6}$ alkyl group such as benzyl, phenethyl etc., and the like) and the like. Examples of the "substituent" of the "aralkyl group optionally having substituent(s)" include substituents similar to the "substituent" of the above-mentioned "alkyl group optionally having substituent(s)", and the number of substituents is about 1 to 4. When the number of the substituents is two or more, each substituent may be the same or different.

Examples of the "acyl group" for $R^1$ include the "acyl group" described as a substituent for the above-mentioned ring A and the like.

Examples of the "acyloxy group" for $R^1$ include the "acyloxy group" described as a substituent for the above-mentioned ring A and the like.

Preferable $R^1$ is a hydrogen atom.

Examples of the "alkyl group optionally having substituent(s)" for $R^2$, $R^3$ or $R^4$ include the "alkyl group optionally having substituent(s)" described as a substituent for the above-mentioned ring A and the like.

Examples of the "alkoxy group optionally having substituent(s)" for $R^2$, $R^3$ or $R^4$ include the "alkoxy group optionally having substituent(s)" described as the substituent for the above-mentioned ring A and the like.

Examples of the "amino group optionally having substituent(s)" for $R^2$, $R^3$ or $R^4$ include an amino group, a mono-$C_{1-6}$ alkylamino group (e.g., methylamino, ethylamino etc.), a mono-$C_{6-14}$ arylamino group (e.g., phenylamino, 1-naphthylamino, 2-naphthylamino etc.), a di-$C_{1-6}$ alkylamino group (e.g., dimethylamino, diethylamino etc.), a di-$C_{6-14}$ arylamino group (e.g., diphenylamino etc.) and the like.

Preferable $R^2$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group. More preferable $R^2$ is a $C_{1-3}$ alkyl group or a $C_{1-3}$ alkoxy group.

Preferable $R^3$ is a hydrogen atom, a $C_{1-6}$ alkoxy-$C_{1-6}$ alkoxy group or an optionally halogenated $C_{1-6}$ alkoxy group. More preferable $R^3$ is a $C_{1-3}$ alkoxy group which is optionally halogenated or substituted by a $C_{1-3}$ alkoxy group.

Preferable $R^4$ is a hydrogen atom or $C_{1-6}$ alkyl group. More preferable $R^4$ is a hydrogen atom or a $C_{1-3}$ alkyl group (particularly a hydrogen atom).

Preferable Y is a nitrogen atom.

Preferable compound of the formula (I) is a compound wherein ring A is a benzene ring optionally having substituent(s) selected from a halogen atom, an optionally halogenated $C_{1-4}$ alkyl group, an optionally halogenated $C_{1-4}$ alkoxy group and a 5- or 6-membered heterocyclic group, $R^1$ is a hydrogen atom, $R^2$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group, $R^3$ is a hydrogen atom, a $C_{1-6}$ alkoxy-$C_{1-6}$ alkoxy group or an optionally halogenated $C_{1-6}$ alkoxy group, $R^4$ is a hydrogen atom or a $C_{1-6}$ alkyl group, and Y is a nitrogen atom.

Of compound (I), a compound represented by the formula (Ia):

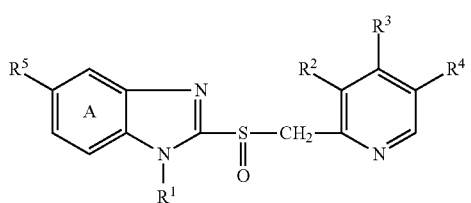

wherein $R^1$ is a hydrogen atom, $R^2$ is a $C_{1-3}$ alkyl group or a $C_{1-3}$ alkoxy group, $R^3$ is a $C_{1-3}$ alkoxy group optionally halogenated or substituted by a $C_{1-3}$ alkoxy group, $R^4$ is a hydrogen atom or a $C_{1-3}$ alkyl group, and $R^5$ is a hydrogen atom, an optionally halogenated $C_{1-3}$ alkoxy group or a pyrrolyl group (e.g., 1-, 2- or 3-pyrrolyl group).

In the formula (Ia), a compound wherein $R^1$ is a hydrogen atom, $R^2$ is a $C_{1-3}$ alkyl group, $R^3$ is an optionally halogenated $C_{1-3}$ alkoxy group, $R^4$ is a hydrogen atom, and $R^5$ is a hydrogen atom or an optionally halogenated $C_{1-3}$ alkoxy group is particularly preferable.

Specific examples of compound (I) include the following compounds.

2-[[[3-Methyl-4-(2,2,2-trifluoroethoxy)-2-pyridinyl]methyl]sulfinyl]-1H-benzimidazole, 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole and the like.

Of these compounds, 2-[[[3-methyl-4-(2,2,2-trifluoroethoxy)-2-pyridinyl]methyl]sulfinyl]-1H-benzimidazole (lansoprazole) is preferable.

Compound (I) may be a racemate or an optically active form such as R-form, S-form and the like. For example, compound (I) may be an optically active form such as (R)-2-[[[3-methyl-4-(2,2,2-trifluoroethoxy)-2-pyridinyl]methyl]sulfinyl]-1H-benzimidazole and the like. In addition, the optically active form is preferable.

As a salt of compound (I) or an optically active form thereof, a pharmaceutically acceptable salt is preferable. For example, salts of compound (I) or an optically active form thereof with an inorganic base, an organic base and a basic amino acid, and the like can be mentioned.

Preferable examples of the salt with inorganic base include alkali metal salts such as sodium salt, potassium salt and the like; alkaline earth metal salts such as calcium salt, magnesium salt and the like; ammonium salt and the like.

Preferable examples of the salt with organic base include salts with alkylamine (trimethylamine, triethylamine etc.), heterocyclic amine (pyridine, picoline etc.), alkanolamine (ethanolamine, diethanolamine, triethanolamine etc.), dicyclohexylamine, N,N'-dibenzylethylene diamine and the like.

Preferable examples of the salt with basic amino acid include salts with arginine, lysine, ornithine and the like.

Of these, preferred is an alkali metal salt or an alkaline earth metal salt. Particularly, a sodium salt is preferable.

Compound (I) can be produced by a method known per se, for example, the methods described in JP-A-61-50978, U.S. Pat. No. B-4,628,098, JP-A-10-195068, WO98/21201 and the like or a method analogous thereto.

The optically active form of compound (I) can be obtained by a method such as an optical resolution method (fractional recrystallization, chiral column method, diastereomer method, a method using microorganism or enzyme etc.), asymmetric oxidation and the like. For example, a lansoprazole R form can be produced according to the methods described in WO00/78745, WO01/83473, WO01/87874 and WO02/44167.

The PPI to be used in the present invention is preferably selected from benzimidazole compounds having an antiulcer activity such as lansoprazole, omeprazole, rabeprazole, and pantoprazole, and optically active forms thereof and pharmaceutically acceptable salts thereof.

(2)-2: "Enteric Micro Granules Containing PPI"

In the present invention, the "enteric micro granules containing PPI" means micro granules wherein a "composition containing PPI" is coated with an enteric coating layer.

The "coating" means also partial coating and adhesion or adsorption in addition to coating the whole surface of an object (e.g., core) which is to be coated.

An average particle size of the "enteric micro granules containing PPI" is generally not more than 400 μm, preferably 300-400 μm.

Aside from the average particle size of the above "micro granules", regarding the maximum particle size, the particle size is generally practically 425 μm or less, and preferably practically 400 μm or less. The particle size is preferably practically 300 to 425 μm, more preferably practically 300 to 400 μm.

"Practically" as used in "the particle size is practically 425 μm or less" and "the particle size is practically 400 μm or less" and the like means that the particles may include a small quantity (about 5 wt % or less) of particles whose particle size is out of above described range, to include the inevitably contaminant particles.

The content of PPI in the aforementioned "composition containing PPI" (composition before coating with enteric coating layer) is, for example, preferably not less than about 5 wt %, more preferably about 10-about 50 wt %, still more preferably about 15-about 50 wt %, particularly preferably about 20-about 50 wt %.

The content of PPI in the orally disintegrating tablet is, for example, preferably not less than about 1 wt %, more preferably not less than about 1.5 wt %, not more than about 10.0 wt %, more preferably not less than about 2.0 wt %, not more than about 8.0 wt %.

The "composition containing PPI" preferably contains a basic inorganic salt to stabilize PPI in the preparation.

The "basic inorganic salt" includes, for example, a basic inorganic salt of sodium, potassium, magnesium and/or calcium, preferably a basic inorganic salt of magnesium and/or calcium. Among others, preferred is a basic inorganic salt of magnesium.

The basic inorganic salt of sodium includes, for example, sodium carbonate, sodium hydrogen carbonate, etc.

The basic inorganic salt of potassium includes, for example, potassium carbonate, potassium hydrogen carbonate, etc.

The basic inorganic salt of magnesium includes, for example, heavy magnesium carbonate, magnesium carbonate, magnesium oxide, magnesium hydroxide, magnesium alumino metasilicate, magnesium silicate, magnesium aluminate, synthetic hydrotalcite [$Mg_6Al_2(OH)_{16}CO_3 4H_2O$], aluminum magnesium hydroxide [$2.5\ MgOAl_2O_3 xH_2O$], etc. Among others, preferred is heavy magnesium carbonate, magnesium carbonate, magnesium oxide, magnesium hydroxide, etc.

The basic inorganic salt of calcium includes, for example, precipitated calcium carbonate, calcium hydroxide, etc.

The preferable examples of the "basic inorganic salt" include heavy magnesium carbonate, magnesium carbonate, magnesium oxide, magnesium hydroxide, etc.

Such basic inorganic salt of magnesium or calcium, etc. only needs to have a basic pH (not less than 7) when it is in the form of a 1% aqueous solution or suspension.

Two or more of these basic inorganic salts (preferably a basic inorganic salt of magnesium, a basic inorganic salt of calcium, etc.) can be used as a mixture. The amount of the basic inorganic salt to be used is appropriately selected depending on the kind of the basic inorganic salt and is, for instance, about 0.3 to about 200 parts by weight, preferably about 1 to about 100 parts by weight, more preferably about 10 to about 50 parts by weight, especially preferably about 20 to about 40 parts by weight, per 100 parts by weight of PPI.

The "composition containing PPI" may contain a water-soluble polymer, and an additive generally used for the production of preparations, such as binder (e.g., HPC), disintegrant (e.g., L-HPC), lubricant (e.g., talc), excipient (e.g., mannitol), colorant (e.g., titanium oxide) and the like. Examples of the additive include those exemplified as the components of the below-mentioned "outer layer". The amount to be added is an amount generally used for the production of preparations. The content of the "binder" is generally about 1-about 20 wt % of the "composition containing PPI". The content of the "lubricant" is generally about 1-about 10 wt % of the "composition containing PPI". The content of the "excipient" is generally 0-about 10 wt % of the "composition containing PPI". The content of the "colorant" is generally 0-about 5 wt % of the "composition containing PPI".

The aforementioned "water-soluble polymer" includes, for example, an ethanol-soluble water-soluble polymer such as a cellulose derivative (e.g., HPC), poly(vinylpyrrolidone), etc.; an ethanol-insoluble water-soluble polymer such as a cellulose derivative (e.g., HPMC, methyl cellulose, carmellose sodium, etc.), sodium polyacrylate, polyvinyl alcohol, sodium alginate, and guar gum, etc.

When such water-soluble polymers are used, the dissolution of PPI can be controlled by employing them in combination with the ethanol-soluble water-soluble polymer and ethanol-insoluble water-soluble polymer or by employing them in combination with some water-soluble polymers having different viscosity.

In the present invention, the "water-soluble polymer" is preferably, a cellulose derivative such as HPC, HPMC, and methyl cellulose, and polyvinyl alcohol. More preferred is a cellulose derivative such as HPC, HPMC.

HPC contains, for example, about 53.4 to about 77.5 wt %, more preferably about 60 to about 70 wt %, of hydroxypropoxyl group. The viscosity of 2 wt % aqueous solution of HPC at 20° C. is generally about 1 to about 150,000 cps (centipoise). As such HPC, the Japanese Pharmacopoeia hydroxypropylcellulose and the like are used (hereinafter the viscosity of HPC is always the value of 2 wt % aqueous solution at 20° C.).

HPMC is mixed ether wherein a methoxy group and a hydroxypropoxy group are bonded. The content of the methoxy group of HPMC is, for example, about 19-about 30 wt %, and the content of the hydroxypropoxy group is, for example, about 4-about 12 wt %. The viscosity of 2 wt % aqueous solution of HPMC at 20° C. is generally about 1-about 40000 centi stokes. As such HPMC, The Japanese Pharmacopoeia hydroxypropylmethylcellulose 2208, The Japanese Pharmacopoeia hydroxypropylmethylcellulose 2906 and The Japanese Pharmacopoeia hydroxypropylmethylcellulose 2910 and the like are used. One or more kinds of HPMC can be used by mixing.

The content of a water-soluble polymer such as HPC and/or HPMC and the like is generally about 0.1-about 50 wt %, preferably about 1-about 30 wt %, of the "composition containing PPI" (composition before coating with enteric coating layer), since dissolution property of PPI in the composition containing PPI can be controlled and a high content of PPI can be maintained.

Examples of the "enteric coating layer" for coating the "composition containing PPI" include aqueous enteric polymer bases such as cellulose acetate phthalate (CAP (trade name; manufactured by Aquateric FMC)), hydroxypropylmethylcellulose phthalate (HP-55 (trade name; manufactured by Shin-Etsu Chemical Co., Ltd.)), hydroxymethylcellulose acetate succinate, methacrylic acid copolymer (e.g., methacrylic acid copolymer LD (Eudragit L30D-55 (trade name; manufactured by EVONIK INDUSTRIES)), Kollicoat MAE30DP (trade name; manufactured by BASF), Polyquid PA30 (trade name; manufactured by Sanyo Chemical Industries Ltd.) and the like), carboxymethylethylcellulose, shellac and the like; sustained-release bases such as methacrylate copolymer (e.g., ethyl acrylate-methyl methacrylate copolymer (Eudragit NE30D (trade name; manufactured by EVONIK INDUSTRIES)), Ammonioalkyl Methacrylate Copolymer Dispersion, Type A (Eudragit RL30D (trade name; manufactured by EVONIK INDUSTRIES)), aminoalkylmethacrylate copolymer RS (Eudragit RS30D (trade name; manufactured by EVONIK INDUSTRIES)) and the like) and the like; water-soluble polymers such as ethanol-soluble water-soluble polymer (e.g., cellulose derivatives such as HPC and the like, polyvinylpyrrolidone and the like), ethanol-insoluble water-soluble polymer (e.g., cellulose derivatives such as HPMC, methylcellulose, carmellose sodium and the like, sodium polyacrylate, polyvinyl alcohol, sodium alginate, guar gum and the like) and the like; plasticizers such as triethyl citrate, polyethylene glycol (e.g., polyethylene glycol 6000), acetylated monoglyceride, triacetin, castor oil and the like, corrigents such as citric anhydride and the like, lubricants such as glycerol monostearate, polysorbate 80 and the like, colorants such as yellow ferric oxide, red ferric oxide, titanium oxide and the like, and the like. These may be used alone or two or more kinds thereof may be used in combination.

As the aforementioned "aqueous enteric polymer base", a methacrylic acid copolymer such as methacrylic acid copolymer LD and the like is preferable. The content of the "aqueous enteric polymer base" is generally about 40-about 90 wt % of the "enteric coating layer".

As the aforementioned "sustained-release base", methacrylate copolymers such as ethyl acrylate-methyl methacrylate copolymer and the like are preferable. The content of the "sustained-release base" is generally about 1-about 20 wt % of the "enteric coating layer". The content of the "sustained-release base" is generally about 5-about 30 parts by weight, preferably about 5-about 15 parts by weight, per 100 parts by weight of the aqueous enteric polymer base.

The content of the aforementioned "plasticizer" is generally about 2-about 30 wt % of the "enteric coating layer". The content of the "plasticizer" is preferably about 5-about 30 parts by weight per 100 parts by weight of the aqueous enteric polymer base.

The content of the aforementioned "corrigent" is generally 0-about 5 wt % of the "enteric coating layer".

The content of the aforementioned "lubricant" is generally about 1-about 10 wt % of the "enteric coating layer".

The content of the aforementioned "colorant" is generally 0-about 5 wt % of the "enteric coating layer".

The "enteric coating layer" preferably contains an aqueous enteric polymer base and a sustained-release base and, for example, a preferable content ratio of methacrylic acid copolymer such as methacrylic acid copolymer LD and the like, and methacrylate copolymer such as ethyl acrylate-methyl methacrylate copolymer and the like (methacrylic acid copolymer (particularly, methacrylic acid copolymer LD): methacrylate copolymer (particularly, ethyl acrylate-methyl methacrylate copolymer)) is 85:15-95:5, particularly preferably 9:1.

The "composition containing PPI" can be produced by a known granulation method.

The "granulation method" includes, for example, tumbling granulation method (e.g., centrifugal tumbling granulation, etc.), fluid-bed granulation method (e.g., tumbling fluid-bed granulation, fluidized granulation, etc.), stirring granulation method and the like. Among others, preferred is fluid-bed granulation method, more preferred is tumbling fluid-bed granulation method.

Concrete example of the "tumbling granulation method" includes a method using "CF apparatus" manufactured by Freund Industrial Co., Ltd. and the like. Concrete examples of the "tumbling fluid-bed granulation method" include methods using "SPIR-A-FLOW" manufactured by Freund Industrial Co., Ltd., "Multiplex" manufactured by Powrex Corp., "New-Marumerizer" manufactured by Fuji Paudal Co., Ltd., and the like. The method for spraying the mixed liquid mentioned below can be suitably selected in accordance with the kind of granulator, and may be, for example, any one of a top spray method, a bottom spray method, a tangential spray method, and the like. Among others, a tangential spray method is preferred.

The "composition containing PPI" is produced by, for example, coating a core containing crystalline cellulose and lactose with PPI.

For example, employed is a method described in JP-A-5-92918 (coating method), which comprises coating a core comprising crystalline cellulose and lactose with PPI, if necessary together with a basic inorganic salt, binders, lubricants, excipients, a water-soluble polymer, etc. (hereinafter, may be abbreviated to "coating layer"). For example, employed is a method which comprises coating a core with PPI and a basic inorganic salt, and then further with binders, lubricants, excipients, a water-soluble polymer, etc.

The average particle size of the "cores" is about 250 µm or less, preferably about 50 to about 250 µm, more preferably about 100 to about 250 µm, especially preferably about 100 to about 200 µm. The "cores" having the above average particle size include particles which all pass through a sieve No. 50 sieve (300 µm), particles where about 5 w/w % or less of the total remain on a sieve No. 60 sieve (250 µm), and particles where about 10 w/w % or less of the total pass through a sieve No. 282 sieve (53 µm). The specific volume of the "core" is about 5 ml/g or less, preferably about 3 ml/g or less.

Examples of the "core" include (1) a spherical granulated product comprising crystalline cellulose and lactose, (2) a spherical granulated product being about 150 to about 250 µm and comprising crystalline cellulose (Avicel SP, manufactured by Asahi Chemical Co., Ltd.), (3) a stirring granulated product being about 50 to about 250 µm and comprising lactose (9 parts) and pregelatinized starch (1 part), (4) a micro particle being about 250 µm or less classified as a spherical granule composed of crystalline cellulose described in JP-A-61-213201, (5) a processed product such as wax formed to a sphere by spray chilling or melting granulation, (6) a processed product such as gelatin beads comprising oil component, (7) calcium silicate, (8) starch, (9) a porous particle such as chitin, cellulose, chitosan, etc, and (10) a bulk product such as granulated sugar, crystalline lactose, crystalline cellulose or sodium chloride, and processed preparations thereof. Further, these cores may be produced in accordance with per se known grinding method or granulation method, and sifted to prepare the particles having the desired particle size.

The above "spherical granulated product comprising crystalline cellulose and lactose" includes, for example, (i) a spherical granulated product being about 100 to about 200 µm and comprising crystalline cellulose (3 parts) and lactose (7 parts) [e.g., Nonpareil 105 (70-140) (particle size of 100 to 200 µm), manufactured by Freund Industrial Co., Ltd.], (ii) a spherical granulated product being about 150 to about 250 µm and comprising crystalline cellulose (3 parts) and lactose (7 parts) [e.g., Nonpareil NP-7:3, manufactured by Freund Industrial Co., Ltd.], (iii) a spherical granulated product being about 100 to about 200 µm and comprising crystalline cellulose (4.5 parts) and lactose (5.5 parts) [e.g., Nonpareil 105T (70-140) (particle size of 100 to 200 µm), manufactured by Freund Industrial Co., Ltd.], (iv) a spherical granulated product being about 150 to about 250 µm and comprising crystalline cellulose (5 parts) and lactose (5 parts) [e.g., Nonpareil NP-5:5, manufactured by Freund Industrial Co., Ltd.], and the like.

In order to produce a preparation which is superior in dissolution while retaining suitable strength, the "core" includes, for example, preferably the spherical granulated product comprising crystalline cellulose and lactose, more preferably the spherical granulated material comprising crystalline cellulose and lactose and containing 50 wt % or more of lactose. Among others, preferred is a core comprising 40 to 50 wt % of crystalline cellulose and 50 to 60 wt % of lactose.

The "core" employed in the present invention is preferably a spherical granulated product comprising crystalline cellulose and lactose, more preferably the spherical granulated product being about 100 to about 200 µm and comprising crystalline cellulose (3 parts) and lactose (7 parts), more preferably the spherical granulated product being about 100 to about 200 µm and comprising crystalline cellulose (4.5 parts) and lactose (5.5 parts).

The "core" may contain PPI. Even when the core does not contain PPI, the releaseability of PPI can be controlled by a coating layer containing PPI.

The "core" may be a powdery core, and is preferably as uniform a sphere as possible to reduce variability of the coating.

The ratio of the "coating layer" to the "core" can be selected within the range in which it is possible to control dissolution of PPI and particle size of the composition, for example, generally about 50 to about 400 parts by weight per 100 parts by weight of the core.

The "coating layer" may be constructed by plural layers. At least one layer of the plural layers must contain PPI. The combination of various layers such as a coating layer not containing the active ingredient, a base coating layer, and an enteric coating layer which constitute the coating layer can be suitably selected.

When the "core" is coated, for example, PPI and the water-soluble polymer can be used as a mixed liquid. The liquid may be a solution or a dispersion, and can be prepared by using an organic solvent such as water or ethanol or an admixture thereof.

The concentration of the water-soluble polymer in the liquid varies according to the proportion of PPI and the additives, and is generally about 0.1 to about 50 wt %, preferably about 0.5 to about 10 wt %, in order to retain the binding strength of PPI to the core and maintain the viscosity of the liquid so as not to reduce the workability.

Where the coating layer comprises plural layers, the concentration of PPI in each layer may be changed successively or gradually by selecting for the content proportion or viscosity of the water-soluble polymer or by successive coating with mixed liquid varying in the proportion of PPI and the other additives. In the above case, it may be coated with a mixed liquid in which the content proportion of the water-soluble polymer is out of the range of about 0.1 to about 50 wt %, as long as the coating layer as a whole contains about 0.1 to about 50 wt % of the water-soluble polymer. Further, in forming the inactive coat according to known methods, the coating layer may comprise some layers such that the inactive layer may block each layer containing PPI.

The above-mentioned coated product is dried and sieved to give a composition having a uniform particle size. Since the shape of the composition generally corresponds to the core, an about spherical composition can also be obtained. As the sieve, for example, No. 50 (300 μm) round sieve can be used, and the composition is obtained by passing the product through the No. 50 round sieve.

The "enteric micro granules containing PPI" can be produced according to a granulation method similar to the above, for example, a method which comprises coating a composition containing PPI with an enteric coating layer, in order to protect PPI or to impart enteric dissolution. If necessary, the composition containing PPI coated with an enteric coating layer may be further coated by a water-soluble sugar alcohol, preferably mannitol. In such case, the strength of the orally disintegrating tablet comprising the micro granules is improved.

The "enteric coating layer" is a layer having preferably about 20 to about 70 μm, more preferably about 30 to about 50 μm of thickness and coating the whole surface of the composition containing PPI. Therefore, the smaller the particle size of the composition is, the higher the wt % of the enteric coating layer in the whole micro granule becomes. In the "enteric micro granules containing PPI", the "enteric coating layer" is generally about 30 to about 70 wt %, preferably about 50 to about 70 wt %, of the micro granule as a whole.

The "enteric coating layer" may be constructed by plural (e.g., 2 or 3) layers. For example, employed is a method which comprises coating a composition containing PPI with an enteric coating layer having polyethylene glycol, and then with an enteric coating layer having triethyl citrate. For example, employed is a method which comprises coating a composition containing PPI with an enteric coating layer having polyethylene glycol, and then with an enteric coating layer having triethyl citrate, followed by being coated with an enteric coating layer having polyethylene glycol.

(3) "Additive"

As mentioned above, the orally disintegrating tablet of the present invention contains "enteric-coated micro granules containing acetylsalicylic acid", "enteric-coated micro granules containing PPI" and an "additive". The additive is a component contained in the part other than the "enteric-coated micro granules containing acetylsalicylic acid" and "enteric-coated micro granules containing PPI" (these are also collectively referred to simply as enteric-coated micro granules).

As the "additive", for example, one or more kinds selected from sugar alcohol (particularly, water-soluble sugar alcohol), crystalline cellulose, L-HPC and the like is/are used, and further, binder, acidulant, sweetener, flavor, lubricant, colorant, stabilizer, excipient, disintegrant and the like is/are also used.

The orally disintegrating tablet of the present invention may utilize a foaming power by a reaction between water content such as saliva and the like and a foaming agent to help disintegration. However, to take medicine without water, achieve rapid disintegration, avoid uncomfortable foaming in the mouth and the like, an antacid and a foaming agent are desirably not contained in the part other than the enteric-coated micro granules. Note that magnesium alumino metasilicate (e.g., NeusilinUFL2 (manufactured by Fuji Chemical Industries Co., Ltd.)) having an antacid action and described later as a disintegrant is excluded from the "antacid".

The aforementioned "water-soluble sugar alcohol" means sugar alcohol that requires less than 30 ml of water to dissolve 1 g of sugar alcohol in water by vigorously shaking them for 30 seconds at 20° C. at 5 min intervals in about 30 min.

Examples of the "sugar alcohol (particularly, water-soluble sugar alcohol)" include sorbitol, mannitol, maltitol, reduced starch saccharides, xylitol, reduced paratinose, erythritol and the like. Two or more kinds (preferably 2-3 kinds) thereof may be mixed at an appropriate proportion and used.

The "sugar alcohol (particularly, water-soluble sugar alcohol)" is preferably mannitol, xylitol, erythritol, more preferably mannitol, erythritol, and particularly preferably mannitol. As erythritol, one generally produced from glucose as a starting material by fermentation by yeast and the like, which has a particle size of 50 mesh or below, is used. Erythritol may be a commercially available product (Nikken Chemicals Co., Ltd. etc.).

To achieve sufficient preparation strength and sufficient orally-disintegrating property, the content of the "sugar alcohol (particularly, water-soluble sugar alcohol)" in the orally disintegrating tablet of the present invention is generally about 40-about 90 wt %, preferably about 50-about 90 wt %, more preferably about 50-about 80 wt %, of the total weight of the components contained in the part other than the enteric-coated micro granules.

The aforementioned "crystalline cellulose" may be any as long as it is obtained by partially depolymerizing α-cellulose, followed by purification. It also includes those called microcrystalline cellulose. Specific examples of crystalline cellulose include CEOLUS KG801 (manufactured by Asahi Kasei Chemicals Co., Ltd.), Avicel PH101, Avicel PH102, Avicel PH301, Avicel PH302, Avicel RC-591 (crystalline cellulose-carmellose sodium) (all manufactured by FMC BioPolymer) and the like. Preferred is CEOLUS KG801 called high compressibility Avicel. Such crystalline cellulose may be used alone or two or more kinds (preferably 2-3 kinds) thereof may also be used in combination. These crystalline celluloses are commercially available.

The content of the crystalline cellulose is generally about 0-about 30 wt %, preferably about 0-about 20 wt %, more preferably about 0-about 15 wt %, of the total weight of the components contained in the part other than the enteric-coated micro granules in the orally disintegrating tablet of the present invention.

The above-mentioned "L-HPC" means L-HPC wherein the content of hydroxypropoxyl group in hydroxypropylcellulose is about 5.0-about 9.9 wt %, particularly about 5.0-about 7.0 wt %, about 7.0-about 9.9 wt % and the like.

Examples of the L-HPC having an hydroxypropoxyl group content of about 7.0-about 9.9% include LH-22, LH-32 (both Shin-Etsu Chemical Co., Ltd.), a mixture thereof and the like, which are available as commercially available products. Also, they can also be produced by a method known per se, for example, the method described in JP-B-S57-53100 as mentioned below or a method analogous thereto.

Examples of the L-HPC having an hydroxypropoxyl group content of about 5.0-about 7.0% include LH-23, LH-33 (both Shin-Etsu Chemical Co., Ltd.), a mixture thereof and the like. These can be produced by a method known per se, for example, the method described in JP-B-S57-53100 or a method analogous thereto.

The particle size of the "L-HPC having a hydroxypropoxyl group content of about 5.0-about 7.0 wt %" is, for example, about 5-about 60 μm, preferably about 10-about 40 μm, as an average particle size.

Using L-HPC having a relatively large particle size (e.g., L-HPC having an average particle size of about 26-about 40 μm) from among such ranges, a preparation superior in the disintegration property can be produced. On the other hand, using L-HPC having a relatively small particle size (e.g., L-HPC having an average particle size of about 10-about 25 μm), a preparation superior in the preparation strength can be produced.

Thus, the particle size of L-HPC can be appropriately selected according to the characteristic of the desired preparation.

To achieve sufficient orally-disintegrating property and sufficient preparation strength, the content of L-HPC having a hydroxypropoxy group content of about 5.0-about 7.0 wt % and/or L-HPC having a hydroxypropoxy group content of about 7.0-about 9.9 wt % is generally about 0-about 30 wt %, preferably about 0-about 20 wt %, more preferably about 0-about 15 wt %, of the total weight of the components contained in the part other than the enteric-coated micro granules in the orally disintegrating tablet of the present invention.

Examples of the aforementioned "binder" include HPC, HPMC, crystalline cellulose, pregelatinized starch, polyvinylpyrrolidone, gum arabic powder, gelatin, pullulan, L-HPC and the like. When crystalline cellulose is used as the binder, a solid preparation having a higher strength and retaining an excellent orally disintegrating property can be obtained.

Examples of the aforementioned "acidulant" include citric acid (citric anhydride), tartaric acid, malic acid and the like.

Examples of the aforementioned "artificial sweetener" include saccharin sodium, dipotassium glycyrrhetinate, aspartame, stevia, thaumatin and the like.

The aforementioned "flavor" may be any of a synthetic substance and a naturally occurring substance and, for example, lemon, lime, orange, menthol, strawberry and the like can be mentioned.

Examples of the aforementioned "lubricant" include magnesium stearate, sucrose ester of fatty acid, polyethylene glycol, talc, stearic acid, hydrogenated oil and the like.

Examples of the aforementioned "colorant" include food colors such as Food Color Yellow No. 5, Food Color Red No. 2, Food Color Blue No. 2 and the like; food lake colors, red ferric oxide and the like.

Examples of the aforementioned "stabilizer" include the aforementioned basic inorganic salt and the like can be mentioned.

Examples of the aforementioned "excipient" include lactose, sucrose, D-mannitol, starch, corn starch, crystalline cellulose, light anhydrous silicic acid, titanium oxide and the like.

As the aforementioned "disintegrant", those conventionally used in the pharmaceutical field can be used. For example, (1) crospovidone (e.g., Kollidon CL-F (manufactured by BASF)), (2) a disintegrant referred to as superdisintegrant such as croscarmellose sodium (FMC-Asahi Kasei), carmellose calcium (GOTOKU CHEMICAL CO., LTD.) and the like, (3) sodium carboxymethyl starch (e.g., manufactured by Matsutani Chemical Industry Co., Ltd.), (4) L-HPC (e.g., manufactured by Shin-Etsu Chemical Co., Ltd.), (5) cornstarch, (6) magnesium alumino metasilicate (e.g., NeusilinUFL2 (manufactured by Fuji Chemical Industries Co., Ltd.), (7) carmellose and the like can be mentioned. Particularly preferable disintegrant includes, for example, crospovidone and/or magnesium alumino metasilicate and/or carmellose.

The "crospovidone" may be any of crosslinked polymer substances having a chemical name of 1-ethenyl-2-pyrrolidinone homopolymer, including those referred to as polyvinylpolypyrrolidone (PVPP) and 1-vinyl-2-pyrrolidinone homopolymer. Specific examples include Kollidon CL (manufactured by BASF), Polyplasdone XL (manufactured by ISP), Polyplasdone XL-10 (manufactured by ISP), Polyplasdone INF-10 (manufactured by ISP) and the like. The molecular weight generally exceeds 1,000,000.

These disintegrants may be used alone, or two or more kinds of them may be used in combination. For example, crospovidone may be used alone or in combination with other disintegrants.

The content of the disintegrant is generally about 5-about 35 wt %, preferably about 5-about 30 wt %, more preferably about 5-about 25 wt %, of the total weight of the components contained in the part other than the enteric-coated micro granules in the orally disintegrating tablet of the present invention.

(4) Orally Disintegrating Tablet

The "orally disintegrating tablet" of the present invention is produced by a method conventionally used in the pharmaceutical field.

The orally disintegrating tablet of the present invention can be produced by mixing the "enteric-coated micro granules containing PPI", "enteric-coated micro granules containing acetylsalicylic acid" and an "additive" by a method known per se, tableting the mixture and, where necessary, drying same.

The content of the "enteric-coated micro granules containing acetylsalicylic acid" in the orally disintegrating tablet of the present invention is generally about 10-about 50 wt %, preferably about 10-about 40 wt %.

The content of the "enteric-coated micro granules containing PPI" in the orally disintegrating tablet of the present invention is generally about 10-about 50 wt %, preferably about 10-about 40 wt %, more preferably about 10-about 30 wt %.

The "mixing" is performed by a mixing method generally used, for example, mixing, kneading, granulation and the like. The "mixing" is performed using an apparatus, such as vertical granulator VG10 (manufactured by Powrex Corporation), a universal kneader (manufactured by HATA IRON WORKS CO., LTD.), a fluidized bed granulator LAB-1, FD-3S (manufactured by Powrex Corporation), a V-type mixer, a tumbler mixer and the like.

The "tableting" is performed by punching at a pressure of 1-80 kN/cm$^2$, 5-50 kN/cm$^2$, preferably 15-40 kN/cm$^2$, by single punch tableting machine (manufactured by KIKUSUI SEISAKUSHO LTD.), rotary tableting machine (manufactured by KIKUSUI SEISAKUSHO LTD.) or rotary multilayer tableting machine (manufactured by HATA IRON WORKS CO., LTD.) and the like. When using a rotary tableting machine, tableting is performed at general rotation, for example, 3-40 min$^{-1}$, preferably 3-30 min$^{-1}$, more preferably 5-25 min$^{-1}$.

The "drying" may be performed by any method generally used for drying preparations, such as vacuum drying, fluid-bed drying and the like. Preferred is drying by vacuum drying.

The tableting method of the orally disintegrating tablet of the present invention may be performed at room temperature or a temperature above room temperature. The "room temperature" refers to a temperature of the room where tableting is performed for general production of tablets, which is generally about 20° C.-about 23° C. That is, the "temperature above room temperature" refers to a temperature exceeding this temperature, where the lower limit is preferably about 25° C. While the temperature varies depending on the starting material powder, granule and the like to be used, it is generally preferably about 25° C.-about 50° C. The temperature can be changed according to the quality of the desired tablet.

The orally disintegrating tablet of the present invention may be a core tablet or a film-coated agent, with preference given to a core tablet. In the present specification, the "core tablet" means a tablet free of a coating treatment such as film coating and the like on the surface of the orally disintegrating tablet obtained in the tableting step.

The weight of the orally disintegrating tablet of the present invention is generally about 500 mg-about 1200 mg.

The "orally disintegrating tablet" of the present invention shows rapid oral disintegration property or dissolution property, and appropriate preparation strength.

The oral disintegration time (a time until an orally disintegrating tablet is completely disintegrated with saliva in the oral cavity of a healthy adult man or woman) of the orally disintegrating tablet of the present invention is generally within about 60 seconds, preferably within about 50 seconds, more preferably within about 45 seconds.

Furthermore, the disintegration time of the orally disintegrating tablet of the present invention (time until complete disintegration of the orally disintegrating tablet in a disintegration test performed at a solution temperature of 37±2° C. using the disintegration test apparatus described in the Japanese Pharmacopeia and water as a test solution) is within about 120 seconds, preferably within about 100 seconds, more preferably within about 80 seconds.

In addition, the orally disintegrating tablet of the present invention has an appropriate hardness that prevents damage in a preparation step or a distribution process. The tablet strength (value measured by a tablet hardness meter) is generally about 30-about 120 N, more preferably about 40-about 120 N.

The orally disintegrating tablet of the present invention has a friability of generally not more than 1%, preferably not more than 0.5%.

The orally disintegrating tablet of the present invention can show an acid resistance rate (dissolution rate of the main drug from the enteric-coated micro granules) of both acetylsalicylic acid and PPI of not more than 10%, preferably not more than 8%, more preferably not more than 5%.

In the present DESCRIPTION, the acid resistance rate means a value obtained by performing a dissolution test according to the Japanese Pharmacopoeia Dissolution Test Method 2 by using 0.1N HCl (500 mL) at 75 rpm for 1 hr, collecting the test solution, filtering same with a 0.45 μm membrane filter, measuring the absorbance and calculating the dissolution rate of the drug in 0.1N HCl.

The orally disintegrating tablet of the present invention is administered without water or together with water. Examples of an administration method include (1) a method comprising holding the preparation of the present invention in the mouth and not swallowing the preparation as it is, and then dissolving or disintegrating the preparation with a small amount of water or with saliva in the oral cavity without water or (2) a method comprising swallowing a preparation as it is together with water. Alternatively, the tablet of the present invention may be dissolved or disintegrated with water, and then be administered.

Since the orally disintegrating tablet of the present invention contains PPI, it has superior antiulcer activity, gastric acid secretion-inhibitory action, mucosa-protecting action, anti-Helicobacter pylori activity and the like.

On the other hand, since the orally disintegrating tablet of the present invention contains acetylsalicylic acid, it is useful as a prophylactic and/or therapeutic agent for cerebrovascular or circulatory diseases, for example, a thrombus and/or embolization inhibitor for angina pectoris (chronic stable angina pectoris, unstable angina pectoris), myocardial infarction; a prophylactic and/or therapeutic agent for ischemic cerebrovascular disorder (transient ischemic attack (TIA), cerebral infarction); a thrombus and/or embolization inhibitor used after coronary-artery bypass surgery (CABG) or percutaneous transluminal coronary angioplasty (PTCA); or a prophylactic and/or therapeutic agent for Kawasaki disease (including cardiovascular sequelae due to Kawasaki disease). Therefore, the orally disintegrating tablet of the present invention can be administered for the treatment or suppression of the onset of gastric ulcer or duodenal ulcer while continuing administration of acetylsalicylic acid. When prophylaxis and/or treatment of such diseases are/is desired, about 10 mg-about 40 mg of PPI is administered per one day, and a low dose of about 70 mg-about 120 mg of acetylsalicylic acid is administered per one day.

Moreover, acetylsalicylic acid can also be used as one kind of non-steroidal anti-inflammatory drug for the treatment of mainly pain, fever and inflammation. Non-steroidal anti-inflammatory drug may cause gastric ulcer or duodenal ulcer. Particularly, in the treatment of rheumatoid arthritis, osteoarthritis and the like, discontinuation of administration of non-steroidal anti-inflammatory drug may be difficult, since it markedly degrades the QOL. In such cases, the orally disintegrating tablet of the present invention can be administered for the treatment or suppression of the onset of gastric ulcer or duodenal ulcer while continuing administration of a non-steroidal anti-inflammatory drug.

When such treatment is desired, about 10 mg-about 40 mg of PPI is administered per one day, and about 240 mg-about 400 mg of acetylsalicylic acid is administered per one day.

Therefore, such orally disintegrating tablet of the present invention is useful as a low toxic and safe combination drug of PPI and acetylsalicylic acid.

The orally disintegrating tablet of the present invention can be orally administered to a mammal (e.g., human, monkey, sheep, horse, dog, cat, rabbit, rat, mouse and the like) for suppression of thrombus and/or embolization in cerebrovascular or circulatory diseases, prophylaxis or treatment of ulcer caused by non-steroidal anti-inflammatory agent; and the like.

In addition to the above-mentioned objects, for eradication or aid of eradication of Helicobacter pylori, the orally disintegrating tablet of the present invention may be used in combination with a penicillin antibiotic (e.g., amoxicillin and the like) and an erythromycin antibiotic (e.g., clarithromycin and the like).

The daily dose of the orally disintegrating tablet of the present invention varies depending on the severity of symptom, the age, sex and body weight of the subject of administration, the timing and interval of administration, the kind of the active ingredient and the like, and is not particularly limited. The orally disintegrating tablet of the present invention may be administered once a day or in 2 or 3 portions a day.

EXAMPLE

The present invention is explained in more detail in the following by referring to Reference Example, Examples and evaluation (Experimental Examples), which are not to be construed as limitative.

The compositions of the orally disintegrating tablets shown in the below-mentioned Examples 1 and 2 are shown in Table 1.

TABLE 1

| component name | Example 1 formulation amount (mg per tablet) | Example 2 formulation amount (mg per tablet) |
|---|---|---|
| acetylsalicylic acid (granules, Rhodine 3118) | 100.0 | |
| acetylsalicylic acid (powder) | | 100.0 |
| Nonpareil105T | | 65.0 |
| mannitol | | 7.0 |
| L-HPC (LH-32) | | 14.0 |
| HPMC (TC-5E) | | 14.0 |
| total of acetylsalicylic acid-containing micro granules | 100.0 | 200.0 |
| methacrylic acid copolymer LD (Eudragit L30D-55) (solid content/suspension) | 23.12/77.08 | 109.18/363.95 |
| ethyl acrylate-methyl methacrylate copolymer (Eudragit NE30D) (solid content/suspension) | 2.57/8.55 | 27.30/90.99 |
| glycerol monostearate | 1.55 | 6.83 |
| citric anhydride | 0.03 | 0.30 |
| polysorbate 80 | 0.61 | 2.74 |
| triethyl citrate | 5.13 | 13.65 |
| total of acetylsalicylic acid enteric-coated micro granules | 133.0 | 360.0 |
| lansoprazole enteric-coated micro granules | 135.0 | 135.0 |
| mannitol (PEARLITOL200SD) | 254.0 | |
| mannitol | | 358.82 |
| carmellose | 60.0 | |
| L-HPC (LH-33) | | 52.37 |
| crystalline cellulose (KG-802) | | 52.37 |
| crospovidone (Polyplasdone XL-10) | | 26.20 |
| aspartame | 6.0 | |
| citric anhydride | 6.0 | 5.23 |
| magnesium stearate | 6.0 | |
| sterile talc | | 10 |
| total of orally disintegrating tablet | 600 | 1000 |

In the Table, Rhodine 3118 (manufactured by Rhodia); Nonpareil105T (manufactured by Freund Corporation); L-HPC (LH-32), HPMC (TC-5E), L-HPC (LH-33) (all manufactured by Shin-Etsu Chemical Co., Ltd.); Eudragit L30D-55, Eudragit NE30D (both manufactured by EVONIK INDUSTRIES); PEARLITOL 200SD (manufactured by ROQUETTE); Polyplasdone XL-10 (manufactured by ISP) are trade names.

Example 1

(i) Production of Lansoprazole Enteric-Coated Micro Granules Lansoprazole-Containing Micro Granules Nonpareil 105 (trade name 41.6 kg) was charged in a tumbling fluid-bed coating granulator (POWREX CORPORATION, MP-400), and a lansoprazole-containing coating solution prepared in advance, which had the following composition, was sprayed for coating. Furthermore, an intermediate layer coating solution prepared in advance, which had the following composition, was sprayed for coating. After completion of the coating, the granules were dried to give lansoprazole-containing micro granules (132 kg).

[Lansoprazole-Containing Coating Solution]

| lansoprazole | 39.60 kg |
|---|---|
| magnesium carbonate | 13.20 kg |
| low-substituted hydroxypropylcellulose | 6.60 kg |
| hydroxypropylcellulose | 13.20 kg |
| (purified water) | (185 L) |

[Intermediate Layer Coating Solution]

| hydroxypropylmethylcellulose | 9.24 kg |
|---|---|
| low-substituted hydroxypropylcellulose | 6.60 kg |
| sterile talc | 3.96 kg |
| titanium oxide | 3.96 kg |
| mannitol | 9.24 kg |
| (purified water) | (99.0 L) |

Lansoprazole Enteric-Coated Micro Granules

Lansoprazole-containing micro granules (44.0 kg) were charged in a tumbling fluid-bed coating granulator (manufactured by POWREX CORPORATION, MP-400), enteric coating solution 1 prepared in advance, which had the following composition, enteric coating solution 2 prepared in advance, which had the following composition, and an overcoating solution prepared in advance, which had the following composition were sprayed for coating. After completion of the coating, drying was performed to give lansoprazole enteric-coated micro granules (about 110 kg) were obtained.

[Glycerol Monostearate Solution]

| glycerol monostearate | 3.150 kg |
|---|---|
| polysorbate 80 | 0.945 kg |
| yellow ferric oxide | 0.0315 kg |
| red ferric oxide | 0.0315 kg |
| (purified water) | (63 L) |

[Enteric Coating Solution 1]

| Eudragit L30D-55 | 9.615 kg solid amount |
|---|---|
| (trade name; EVONIK INDUSTRIES) | (32.05 kg) (liquid amount) |

-continued

| | |
|---|---|
| Eudragit NE30D (trade name; EVONIK INDUSTRIES) | 1.071 kg solid amount (3.570 kg) (liquid amount) |
| polyethylene glycol 6000 | 1.071 kg |
| citric anhydride | 0.0126 kg |
| (purified water) | (31.8 L) |
| glycerol monostearate solution | 13.4 kg (liquid amount) |

[Enteric Coating Solution 2]

| | |
|---|---|
| Eudragit L30D-55 (trade name; EVONIK INDUSTRIES) | 35.28 kg solid amount (117.6 kg) (liquid amount) |
| Eudragit NE30D (trade name; EVONIK INDUSTRIES) | 3.918 kg solid amount (13.06 kg) (liquid amount) |
| triethyl citrate | 7.854 kg |
| citric anhydride | 0.021 kg |
| (purified water) | (9.33 L) |
| glycerol monostearate solution | 53.7 kg (liquid amount) |

[Overcoating Solution]

| | |
|---|---|
| mannitol | 4.200 kg |
| (purified water) | (25.2 L) |

(ii) Production of Acetylsalicylic Acid Enteric-Coated Micro Granules (1) Preparation of Acetylsalicylic Acid Composition Granulated acetylsalicylic acid (Rhodine3118, (trade name; manufactured by Rhodia)) was screened to give acetylsalicylic acid in 16-32 mesh fractions.

(2) Preparation of Enteric Coating Solution

Polysorbate 80 (4.8 g) was dissolved in water (567.6 g), heated to 70° C., and glycerol monostearate (12.2 g) was dispersed in a dispersion machine to give a glycerol monostearate dispersion. Thereto were added methacrylic acid copolymer LD (Eudragit L30D-55 (trade name; manufactured by EVONIK INDUSTRIES), 607.4 g (solid amount 182.2 g)), ethyl acrylate-methyl methacrylate copolymer (Eudragit NE30D (trade name; manufactured by EVONIK INDUSTRIES), 67.4 g (solid amount 20.2 g)), citric anhydride (0.02 g) and triethyl citrate (40.4 g) and mixed to give an enteric coating solution.

(3) Preparation of Acetylsalicylic Acid Enteric-Coated Micro Granules

Using a fine particle coating apparatus (improved Wurster), acetylsalicylic acid (400 g) obtained in (1) was coated with the enteric coating solution obtained in (2) such that the solid content of the enteric coating component was 33 parts by weight per 100 parts by weight of acetylsalicylic acid, whereby acetylsalicylic acid enteric-coated micro granules (fine particles coating acetylsalicylic acid) were obtained.

(iii) Preparation of Orally Disintegrating Tablet

Lansoprazole enteric-coated micro granules (27 g) obtained in (i), acetylsalicylic acid enteric-coated micro granules (26.6 g) obtained in (ii), granulated mannitol (PEARLITOL200SD (trade name; ROQUETTE)) (50.8 g), carmellose (12 g), citric anhydride finely divided powder (1.2 g), aspartame (1.2 g), and magnesium stearate (1.2 g) were mixed to give a mixed powder. The mixed powder was tableted by an AUTOGRAPH using a 13 mm diameter flat plane punch at tableting pressure 10 KN to give a multiple-unit type orally disintegrating tablet containing lansoprazole enteric-coated micro granules and acetylsalicylic acid enteric-coated micro granules.

Example 2

(i) Production of Lansoprazole Enteric-Coated Micro Granules

The micro granules were obtained in the same manner as in Example 1.

(ii) Preparation of Acetylsalicylic Acid Composition

An acetylsalicylic acid powder was pulverized in a jet mill to give an acetylsalicylic acid finely divided powder having an average particle size of about 8 μm.

(iii) Preparation of Acetylsalicylic Acid-Containing Micro Granules

Nonpareil105T (trade name) (520 g) was charged in a tumbling fluid-bed coating granulator (manufactured by POWREX CORPORATION, MP-01), and spray-coated with a previously-prepared acetylsalicylic acid-containing coating solution having the following composition. After the completion of coating, the granules were dried to give acetylsalicylic acid-containing micro granules.

[Acetylsalicylic Acid-Containing Coating Solution]
acetylsalicylic acid 800 g
mannitol 56 g
low-substituted hydroxypropylcellulose 112 g
hydroxypropylmethylcellulose 112 g
(purified water) (4.32 L)

(iv) Preparation of Acetylsalicylic Acid Enteric-Coated Micro Granules

Acetylsalicylic acid-containing micro granules (200 g) were charged in a tumbling fluid-bed coating granulator (manufactured by Freund Corporation, SPIR-A-FLOW), and spray-coated with a previously-prepared enteric coating solution having the following composition, until the solid content of the enteric coating component became 80 parts by weight per 100 parts by weight of acetylsalicylic acid-containing micro granules. The granules were dried to give acetylsalicylic acid enteric-coated micro granules.

[Glycerol Monostearate Solution]
glycerol monostearate 8.5 g
polysorbate 80 3.4 g
(purified water) (350 mL)
[Enteric Coating Solution]
Eudragit L30D-55 (trade name; EVONIK INDUSTRIES)
   136.5 g solid amount
   (454.9 g) (liquid amount)
Eudragit NE30D (trade name; EVONIK INDUSTRIES)
   34.1 g solid amount
   (113.7 g) (liquid amount)
citric anhydride 0.38 g
(purified water) (51.9 mL)
triethyl citrate 17.1 g
glycerol monostearate solution 361.9 g (total amount)

(v) Production of Outer Layer Component Granulated Powder

Mannitol (2743 g), low-substituted hydroxypropylcellulose (432 g), crystalline cellulose (432 g), and crospovidone (216 g) were charged in a fluid bed granulator (MP-10 TOKU-2 type, POWREX CORPORATION), and the mixture was granulated by spraying an aqueous solution of mannitol (216 g) and citric acid (43.2 g) in purified water (1440 g) and dried to give a granulated powder (4082 g).

[Composition in 314.07 mg of Outer Layer Component Granulated Powder]
mannitol 227.66 mg
low-substituted hydroxypropylcellulose 33.23 mg
crospovidone 16.62 mg crystalline cellulose 33.23 mg
citric anhydride 3.32 mg
total 314.07 mg (vi) Preparation of Orally Disintegrating Tablet The lansoprazole enteric-coated micro granules (67.5 g) obtained in (i), the acetylsalicylic acid enteric-coated micro granules (180 g) obtained in (iv), the outer layer component granulated powder (247.5 g) obtained in (v), and sterile talc (5 g) were mixed to give a mixed powder. The mixed powder was tableted by a compact tableting machine using a 13 mm diameter flat plane punch at tableting pressure 20 KN to give a multiple-unit type orally disintegrating tablet containing lansoprazole enteric-coated micro granules and acetylsalicylic acid enteric-coated micro granules.

Evaluation

The orally disintegrating tablets obtained in Examples 1 and 2 were subjected to a dissolution test using the Japanese Pharmacopoeia 2nd fluid as a test solution and under conditions of Paddle Method 75 rpm, and the dissolution rate of acetylsalicylic acid was evaluated. The results are shown in Table 2.

The results reveal that not less than 70% of acetylsalicylic acid dissolved in 60 min in both Examples 1 and 2, and that the pharmacological effect of acetylsalicylic acid is expressed stably and rapidly after administration.

TABLE 2

| time lapsed | acetylsalicylic acid dissolution profile (The Japanese Pharmacopoeia 2nd fluid, 75 rpm) | |
|---|---|---|
| | dissolution rate | |
| | Example 1 | Example 2 |
| 15 min | — | 30% |
| 20 min | 30% | — |
| 30 min | — | 65% |
| 40 min | 50% | — |
| 60 min | 70% | not less than 80% |
| 90 min | not less than 85% | — |

INDUSTRIAL APPLICABILITY

According to the present invention, an orally disintegrating tablet showing high stability of the active ingredients, and expressing the pharmacological effect of the active ingredients stably and rapidly after administration can be provided.

This application is based on patent application No. 2013-107072 filed in Japan, the contents of which are encompassed in full herein.

The invention claimed is:

1. A multiple-unit orally disintegrating tablet comprising enteric-coated micro granules containing acetylsalicylic acid, enteric-coated micro granules containing a proton pump inhibitor, and an additive,
   which shows a dissolution rate of acetylsalicylic acid of not less than 70% at the 60-min time point, in a dissolution test using the Japanese Pharmacopoeia 2nd fluid as a test solution and under conditions of Paddle Method 75 rpm,
   wherein an enteric coating layer of the enteric-coated micro granules containing acetylsalicylic acid comprises an aqueous enteric polymer base and a sustained-release base,
   the enteric-coated micro granules containing acetylsalicylic acid have an average particle size of not more than 600 μm,
   the content of the acetylsalicylic acid in the enteric-coated micro granules containing acetylsalicylic acid is about 20-about 80 wt %,
   the additive contains mannitol,
   the content of the mannitol is about 40-about 90 wt % of the total weight of the part of the tablet other than the enteric-coated micro granules containing acetylsalicylic acid and enteric-coated micro granules containing a proton pump inhibitor, and
   the acetylsalicylic acid and the proton pump inhibitor each show an acid resistance rate of not more than 10%.

2. The orally disintegrating tablet according to claim 1, wherein the aqueous enteric polymer base is a methacrylic acid copolymer LD.

3. The orally disintegrating tablet according to claim 1, wherein the sustained-release base is an ethyl acrylate-methyl methacrylate copolymer.

4. The orally disintegrating tablet according to claim 1, wherein the enteric coating layer of the enteric-coated micro granules containing acetylsalicylic acid contains the aqueous enteric polymer base and the sustained-release base at a solid content weight ratio of 80:20-95:5.

5. The orally disintegrating tablet according to claim 1, wherein the content of acetylsalicylic acid is 70 mg-120 mg per tablet.

6. The orally disintegrating tablet according to claim 1, wherein the proton pump inhibitor is lansoprazole, omeprazole, rabeprazole, pantoprazole or an optically active form thereof or a salt thereof.

7. The orally disintegrating tablet according to claim 1, wherein the additive is free of an antacid and a foaming agent.

8. The orally disintegrating tablet according to claim 1, having an oral disintegration time of within about 60 seconds.

* * * * *